(12) United States Patent
Rink et al.

(10) Patent No.: US 6,624,280 B1
(45) Date of Patent: Sep. 23, 2003

(54) OLIGOMERIC AND HIGH-MOLECULAR CONVERSION PRODUCTS OF ALLOPHANIC ACID ESTERS WITH NUCLEOPHILIC COMPOUNDS AND LOW-MOLECULAR, OLIGOMERIC AND HIGH-MOLECULAR COMPOUNDS WITH ALLOPHANATE SIDE AND/OR TERMINAL GROUPS, AND THE USE THEREOF

(75) Inventors: Heinz-Peter Rink, Münster (DE); Werner Jung, Ascheberg (DE); Ulrike Röckrath, Senden (DE); Thomas Savino, Northville, MI (US)

(73) Assignee: BASF Coatings AG, Munster (DE)

( * ) Notice: Subject to any disclaimer, the term of this patent is extended or adjusted under 35 U.S.C. 154(b) by 0 days.

(21) Appl. No.: 09/762,121

(22) PCT Filed: Aug. 27, 1999

(86) PCT No.: PCT/EP99/06327

§ 371 (c)(1),
(2), (4) Date: Mar. 2, 2001

(87) PCT Pub. No.: WO00/12578

PCT Pub. Date: Mar. 9, 2000

(30) Foreign Application Priority Data

Aug. 29, 1998 (DE) .......................................... 198 39 453

(51) Int. Cl.[7] .............................................. C08G 18/10
(52) U.S. Cl. ...................... 528/59; 525/329.9; 525/185; 560/25; 560/115; 560/158
(58) Field of Search .............................. 525/329.9, 185; 560/25, 115, 158; 528/59

(56) References Cited

U.S. PATENT DOCUMENTS

| | | | |
|---|---|---|---|
| 4,710,542 A | 12/1987 | Forgione et al. | 525/127 |
| 4,939,213 A | 7/1990 | Jacobs, III et al. | 525/329.9 |
| 5,084,541 A | 1/1992 | Jacobs, III et al. | 528/45 |
| 5,098,947 A | 3/1992 | Metzger et al. | 524/507 |
| 5,288,865 A | 2/1994 | Gupta | 544/200 |
| 5,336,566 A | 8/1994 | Rehfuss | 428/524 |
| 5,475,073 A | 12/1995 | Guo | 526/333 |
| 5,480,493 A | 1/1996 | Harry, Jr. | 134/4 |
| 5,534,598 A | 7/1996 | Guo | 525/329.2 |

FOREIGN PATENT DOCUMENTS

| | | | |
|---|---|---|---|
| DE | 3634780 C 2 | 2/1990 | C09D/201/06 |
| DE | 196 44 932 A1 | 10/1996 | C08G/18/78 |
| EP | 0 059 400 A2 | 2/1982 | C07C/125/06 |
| EP | 0 079 515 A2 | 11/1982 | C07C/127/22 |
| EP | 0 133 274 A1 | 7/1984 | C07C/125/06 |
| EP | 0 594 068 A1 | 10/1993 | C09D/201/02 |
| EP | 0 594 071 A1 | 10/1993 | C09D/201/02 |
| EP | 0 594 142 A1 | 10/1993 | C98L/57/12 |
| EP | 0 604 922 A1 | 12/1993 | C08K/5/3492 |
| EP | 0 622 387 A1 | 4/1994 | C08G/18/28 |
| EP | WO 94/10211 | 5/1994 | C08F/8/30 |
| EP | WO 94/10212 | 5/1994 | C08F/8/30 |
| EP | WO 94/10213 | 5/1994 | C08F/8/30 |
| EP | 0 708 788 B1 | 1/1995 | C08G/18/08 |
| EP | 0 767 185 A1 | 6/1995 | C08F/21/06 |

OTHER PUBLICATIONS

B.J. Ludwig et al; Carbamate Derivatives; J. Med. Chem., 1969, 12(3), abstract.*
European Polymer Journal, 27. 1991., No. 10, pp. 1039–1044 Kricheldorf et al; Polymers of Carbonic Acid.

* cited by examiner

*Primary Examiner*—Rachel Gorr

(57) ABSTRACT

Oligomeric and high molecular mass products of reaction of alkyl and aryl allophanates with nucleophilic compounds, and also low molecular mass, oligomeric and high molecular mass compounds containing lateral and/or terminal allophanate groups, and also the use of the reaction products and/or of the compounds in coating compositions, adhesives and sealing compounds or for producing films.

17 Claims, No Drawings

OLIGOMERIC AND HIGH-MOLECULAR CONVERSION PRODUCTS OF ALLOPHANIC ACID ESTERS WITH NUCLEOPHILIC COMPOUNDS AND LOW-MOLECULAR, OLIGOMERIC AND HIGH-MOLECULAR COMPOUNDS WITH ALLOPHANATE SIDE AND/OR TERMINAL GROUPS, AND THE USE THEREOF

This application claims priority under 35 USC §120 upon International PCT Application PCT/EP99 filed Aug. 27, 1999 and German Patent Application DE 198 39 453.3, filed Aug. 29, 1998.

The present invention relates to novel oligomeric and high molecular mass products of reaction of allophanic esters with nucleophilic compounds and also to novel low molecular mass, oligomeric and high molecular mass compounds containing lateral and/or terminal allophanate groups. The present invention additionally relates to the use of these reaction products and compounds in coating compositions, films, adhesives, and sealing compounds. The present invention further relates to novel coating compositions, films, adhesives and sealing compounds which comprise the novel oligomeric and/or high molecular mass products of reaction of allophanic esters with nucleophilic compounds and/or the novel low molecular mass, oligomeric and high molecular mass compounds containing lateral and/or terminal allophanate groups. The present invention relates not least to novel processes for preparing these reaction products or compounds.

Clearcoat materials for the automobile sector which comprise oligomers and/or polymers containing lateral and/or terminal carbamate (—O—C(O)—NH$_2$) groups are known from the patents EP-A-0 594 071, EP-A-0 594 068, EP-A-0 594 142, WO 94/10212, WO 94/10211, WO 94/10213, DE-C-36 34 780 and U.S. Pat. No. 5,098,947. They may be prepared by different processes, which are described in these patents. It has, however, proven appropriate to prepare these oligomers and polymers containing lateral and/or terminal carbamate groups by reacting hydroxyl-containing oligomers and polymers with methyl carbamate. In some cases of transcarbamation, however, the reactivity of methyl carbamate is comparatively low, so that relatively high temperatures must be employed in order to obtain higher reaction rates. However, the higher temperatures may cause thermal damage to the products, after which they are no longer suitable for use, for example, in clearcoat materials.

Low molecular mass and oligomeric compounds containing lateral and/or terminal carbamate (—HN—C(O)—O—R) groups are described in the patents U.S. Pat. No. 4,710,542 and EP-B-0 245 700 and also in the article by B. Singh and co-workers, "Carbamylmethylated Melamines, Novel Cross-linkers for the Coatings Industry", in Advanced Organic Coatings Science and Technology Series, 1991, Volume 13, pages 193 to 207. These compounds comprise reaction products of carbamates, especially alkyl carbamates, and melamine resins. These lateral and/or terminal carbamate (—HN—C(O)—O—R) groups are no longer capable of entering into crosslinking reactions with the lateral and/or terminal carbamate (—O—C(O)—NH$_2$) groups. These low molecular mass and oligomeric compounds are therefore referred to, inter alia, as "partially defunctionalized amino resins".

Low molecular mass and oligomeric compounds containing lateral and/or terminal carbamate (—HN—C(O)—O—R—O—C(O)—NH$_2$) groups are described in the patents U.S. Pat. No. 5,336,566 and EP-A-0 622 387. These compounds are prepared from polyisocyanates and hydroxyalkyl carbamates. In particular, they enter into crosslinking reactions with amino resins.

An object of the present invention is to find new oligomeric and high molecular mass reaction products and low molecular mass, oligomeric and high molecular mass compounds which offer an alternative to the existing low molecular mass, oligomeric and high molecular mass reaction products and/or compounds containing lateral and/or terminal carbamate groups and which possess a higher reactivity than these products and compounds while having at least the same advantageous properties as them. The new oligomeric reaction products and/or the new low molecular mass and oligomeric compounds are to be suitable for use as new advantageous crosslinkers, and the new oligomeric and high molecular mass reaction products and the new oligomeric and high molecular mass compounds are to be suitable for use as new advantageous binders for coating compositions, adhesives and sealing compounds, or for the production of films.

A further object of the present invention is to provide new coating compositions, adhesives, sealing compounds and film precursors which have a new crosslinking chemistry and offer an advantageous alternative to the existing systems.

Yet another object of the present invention is to find new, simple and elegant processes for preparing the new oligomeric and high molecular mass reaction products and/or the new low molecular mass, oligomeric and high molecular mass compounds.

We have found, accordingly, the novel oligomeric and high molecular mass products of reaction of allophanic esters with nucleophilic compounds and also the novel low molecular mass, oligomeric and high molecular mass compounds containing lateral and/or terminal allophanate groups.

We have also found the novel coating compositions, films, adhesives and sealing compounds which comprise the novel low molecular mass, oligomeric and/or high molecular mass products of reaction of allophanic esters of nucleophilic compounds and/or the novel low molecular mass, oligomeric and/or high molecular mass compounds containing lateral and/or terminal allophanate groups.

Furthermore, we have found

A) a novel process for preparing the novel oligomeric and high molecular mass products of reaction of allophanic esters with nucleophilic compounds and/or the novel oligomeric and high molecular mass compounds containing lateral and/or terminal allophanate groups by transallophanatization of hydroxyl-containing oligomers and/or polymers (nucleophiles) with alkyl and aryl allophanates, B) a novel process for preparing the novel low molecular mass and oligomeric compounds by reacting amino resins with alkyl and aryl allophanates, and C) another novel process for preparing other novel low molecular mass and oligomeric compounds by reacting polyisocyanates with hydroxyalkyl allophanates.

In the light of the prior art, it was surprising and unforeseeable that the object on which the invention was based might be achieved with the aid of allophanates of the general formula I and allophanate groups of the general formulae II, III and IV:

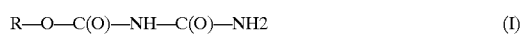

—CH$_2$—NH—C(O)—NH—C(O)—OR$^1$ (III)

—O—R$^2$—O—C(O)—NH—C(O)—NH$_2$ (IV)

In the general formula III, the radical R$^1$ denotes an alkyl or cycloalkyl group, in particular a C$_1$ to C$_{10}$ alkyl group or a C$_5$ to C$_{10}$ cycloalkyl group; examples of suitable such groups for use in accordance with the invention are methyl, ethyl, propyl, isopropyl, n-butyl, isobutyl, tert-butyl, n-pentyl, neopentyl, n-hexyl, 2-methylhexyl, n-heptyl, 2-ethylhexyl, n-octyl, isooctyl, n-nonyl, n-decyl, cyclopentyl, cyclohexyl, cycloheptyl, indenyl or decalinyl radicals;

an aryl group, in particular a phenyl group;

one of the aforementioned radicals containing essentially inert groups which do not react with crosslinking agents or binders; examples of suitable such groups are halogen atoms such as chlorine or fluorine atoms, aromatic radicals, nitro groups or alkyl or aryl ether groups; and also one of the aforementioned groups which have at least one free hydroxyl group, especially those derived from low molecular mass, linear or branched polyols or from cycloaliphatic polyols; examples of suitable polyols are neo-alcohols, butylethyl-1,3-propanediol, 2-methyl-1,3-propane-diol, 1,6-hexeanediol, 1,8-octanediol, 2,4-diethyl-1,3-octanediol, 2-ethyl-1,3-hexanediol, 1,4-dimethylolcyclohexane, trimethylolpropane, glycerol, diglycerol, polyglycerol, pentaerythritol, dipentaerythritol or homopentaerythritol.

In the general formula IV, the radical R$^2$ denotes linear or branched alkanediyl radicals or cycloalkanediyl radicals, especially methylene, ethylene, propylene-1,2-, tetramethylene, penta-methylene, hexamethylene, heptamethylene, cyclo-hexane-1,3-, -1,2- or -1,4-diyl, butylethyl-propane-1,3-diyl, 2-methylpropane-1,3-diyl, 2,4-diethyloctane-1,3-diyl, 2-ethylhexane-1,3-diyl or cyclohexane-1,4-dimethylene radicals;

arylene radicals, especially 1,2-, 1,4- and 1,4-phenylene radicals;

the aforementioned diyl and ylene radicals which carry the abovementioned inert groups which do not react with crosslinking agents or binders; and also diyl radicals which still have at least one free hydroxyl group and are derived from triols and polyols, especially from trimethylolpropane, glycerol, diglycerol, polyglycerol, pentaery-thritol, dipentaerythritol or homopentaerythritol.

With the aid of these allophanates and allophanate. groups, a new kind of crosslinking chemistry is provided which yields results which is equivalent if not superior to those of the crosslinking chemistry based on carbamates and amino resins.

In the text below, for the sake of brevity, the allophanates of the general formula I are referred to as "allophanates I" and the allophanate groups of the general formulae II, III and IV are referred to respectively as "allophanate groups II, III and IV".

Furthermore, in the text below, the novel oligomeric and high molecular mass products of reaction of allophanic esters with nucleophiles are referred to for brevity, respectively, as "oligomeric reaction products of the invention" or "high molecular mass reaction products of the invention", and the novel low molecular mass, oligomeric and high molecular mass compounds which contain lateral and/or terminal allophanate groups are referred to correspondingly, for brevity, as "low molecular mass compounds of the invention", oligomeric compounds of the invention" or "high molecular mass compounds of the invention", respectively.

Moreover, in the text below, for brevity, the novel process for preparing the oligomeric and high molecular mass reaction products and compounds of the invention by transallophanatization is referred to as "process A of the invention", the novel process for preparing the low molecular mass and oligomeric compounds of the invention by reacting amino resins with alkyl and aryl allophanates is referred to as "process B of the invention", and the novel process for preparing the low molecular mass and oligomeric compounds of the invention by reacting polyisocyanates with hydroxyalkyl and hydroxyaryl allophanates is referred to as "process C of the invention".

In the context of the present invention, the terms "low molecular mass", "oligomeric" and "high molecular mass" are used in their familiar signification. In other words, the term "oligomeric" indicates that the compound in question is composed on average of 3 to about 10 repeating identical basic building blocks and thus constitutes an oligomer. Accordingly, the term "high molecular mass" indicates that the compound in question is composed on average of more than 10 repeating identical basic building blocks and thus constitutes a polymer, which if appropriate may also be present in the form of highly crosslinked particles.

The oligomeric and high molecular mass reaction products of the invention are formed by the reaction of nucleophiles with alkyl and aryl allophanates. Depending on the nature of the nucleophile, this may result in a relatively wide variety of functional groups. However, the groups in question in this case may also be the allophanate groups II, III and IV, but in particular the allophanate groups II.

The oligomeric and high molecular mass compounds of the invention are oligomers and polymers which contain the allophanate groups II, III and IV as lateral and/or terminal groups. In accordance with the invention it is of advantage, however, if the oligomeric and high molecular mass compounds of the invention contain only at least two, preferably at least three, of the allophanate groups II.

If the oligomeric and high molecular mass reaction products of the invention comprise the allophanate groups II, III and IV, but especially the allophanate groups II, as lateral and/or terminal groups, the compounds in question are, logically, the oligomeric and high molecular mass compounds of the invention. Since in such cases the preparation of the oligomeric and high molecular mass reaction products of the invention is no different from the preparation of the oligomeric and high molecular mass compounds of the invention, both are dealt with together below under the compounds.

In special cases, it is of advantage in accordance with the invention if the low molecular mass and oligomeric compounds of the invention contain only at least two, in particular at least three, of the allophanate groups III or IV.

Although the preparation of the oligomeric and high molecular mass compounds of the invention containing allophanate groups II may take place in accordance with any desired methods, it is nevertheless of advantage in accordance with the invention to prepare them by process A of the invention. To this end, oligomers and polymers which contain at least two, preferably at least three, primary and/or secondary, but especially primary, hydroxyl groups and which are therefore nucleophiles within the meaning of the present invention are transallophanatized with alkyl and aryl allophanates I at from 30 to 200° C., preferably from 50 to 160° C., with particular preference from 60 to 150° C., and in particular from 80 to 140° C. The reaction is carried out in solution or without solvent, preferably in solution. It is advisable to add customary and known inhibitors such as trialkyl phosphites, especially triisodecyl phosphite, to the reaction mixture. It is also of advantage to use customary and known transesterification catalysts such as tin compounds, especially dibutyltin dioxide.

In the general formula I, the radical R denotes $C_1$ to $C_{10}$alkyl radicals, $C_5$ to $C_{10}$ cycloalkyl radicals or phenyl radicals. Examples of suitable such radicals are set out above in the context of the description of the radical $R^1$ of the formula III. In accordance with the invention, the $C_1$ to $C_5$ alkyl radicals are of advantage in the transallophanatization and are therefore used with preference. Examples of suitable allophanates I for use in accordance with the invention are, accordingly, methyl, ethyl, propyl, butyl, pentyl or phenyl allophanate, of which methyl allophanate and ethyl allophanate are particularly advantageous and are therefore used with particular preference in accordance with the invention.

As oligomers and polymers for use in accordance with the invention which have at least two, preferably at least three, primary and/or secondary, but especially primary, hydroxyl groups (nucleophiles), those which are suitable include, preferably, linear and/or branched and/or block, comb and/or random poly(meth)acrylates, polyesters, polyurethanes, acrylated polyurethanes, acrylated polyesters, polyl-actones, polycarbonates, polyethers, (meth)acrylate-diols, polyureas or oligomeric polyols.

Besides the hydroxyl groups, the oligomers and polymers may include other functional groups such as acryloyl, ether, amide, imide, thio, carbonate or epoxide groups.

These oligomers and polymers are known to the skilled worker, and many suitable compounds are commercially available.

In accordance with the invention, the oligomeric polyols, the polyacrylates, the polyesters and/or the acrylated polyurethanes are of advantage and are therefore used with preference.

Examples of preferred oligomers and polymers for use in accordance with the invention which have at least two, preferably at least three, primary and/or secondary, but especially primary, hydroxyl groups are 1. Oligomeric polyols obtainable by hydroformylation and subsequent hydrogenation from oligomers obtained by metathesis reactions from acyclic monoolefins and cyclic monoolefins; examples of suitable cyclic monoolefins are cyclobutene, cyclopentene, cyclohexene, cyclooctene, cycloheptene, norbornene or 7-oxanorbornene; examples of suitable acyclic monoolefins are present in hydrocarbon mixtures obtained in petroleum processing by cracking ($C_5$ cut); examples of suitable oligomeric polyols for use in accordance with the invention have a hydroxyl number (OHN) of from 200 to 450, a number-average molecular weight $M_n$ of from 400 to 1000 and a mass-average molecular weight $M_w$ of from 600 to 1100;

2. Polyacrylates having a hydroxyl number of from 40 to 240, preferably from 60 to 210, in particular from 100 to 200, an acid number of from 0 to 35, glass transition temperatures of from −35 to +80° C. and number-average molecular weights $M_n$ of from 1500 to 300 000.

The glass transition temperatures of the polyacrylates are determined, as is known, by the nature and amount of the monomers used. The selection of the monomers may be made by the skilled worker with the assistance of the following formula V, by which the glass transition temperatures may be calculated approximately.

$$1/T_g = \sum_{n=1}^{n=x} W_n/T_{g_n} \ ; \ W_n = 1 \quad (V)$$

$T_g$ = glass transition temperature of the polyacrylate resin
$W_n$ = weight fraction of the nth monomer
$T_{g_n}$ = glass transition temperature of the homopolymer of the nth monomer
$x$ = number of different monomers Measures to control the molecular weight (e.g., selection of corresponding polymerization initiators, use of chain transfer agents, or special polymerization processes, etc.) are part of knowledge in the art and need not be elucidated here.

2.1 Particularly preferred polyacrylates are preparable by polymerizing (a1) from 10 to 92, preferably from 20 to 60% by weight of an alkyl or cycloalkyl methacrylate having 1 to 18, preferably 4 to 13 carbon atoms in the alkyl or cycloalkyl radical or mixtures of such monomers, (a2) from 8 to 60, preferably from 12.5 to 50.0% by weight of a hydroxyalkyl acrylate or a hydroxyalkyl methacrylate having 2 to 4 carbon atoms in the hydroxyalkyl radical or mixtures of such monomers, (a3) from 0 to 5, preferably from 0.7 to 3% by weight of acrylic acid or methacrylic acid or mixtures of these monomers, and (a4) from 0 to 50, preferably up to 30% by weight, of ethylenically unsaturated monomers which are different from (a1), (a2) and (a3) but are copolymerizable with (a1), (a2) and (a3), or mixtures of such monomers, to give polyacrylates of the specification indicated above.

Examples of suitable (a1) components are methyl, ethyl, propyl, n-butyl, isobutyl, tert-butyl, pentyl, hexyl, heptyl or 2-ethylhexyl acrylate or methacrylate and also cyclohexyl, tert-butyl-cyclohexyl or isobornyl acrylate or methacrylate.

Examples of suitable (a2) components are hydroxyethyl, hydroxypropyl or hydroxybutyl or hydroxymethylcyclohexyl acrylate or methacrylate or adducts of (meth)acrylic acid and epoxides such as VersaticR acid glycidyl ester.

Examples of suitable (a4) components are vinylaromatics such as styrene, vinyltoluene, alpha-methylstyrene, alpha-ethylstyrene, ring-substituted diethylstyrenes, isopropylstyrene, butylstyrene and methoxystyrenes; vinyl ethers such as ethyl, n-propyl, isopropyl, n-butyl or isobutyl vinyl ether; vinyl esters such as vinyl acetate, vinyl propionate, vinyl butyrate, vinyl pivalate or the vinyl ester of 2-methyl-2-ethylheptanoic acid; or allyl ethers such as trimethylolpropane monoallyl, diallyl or triallyl ether or ethoxylated or propoxylated allyl alcohol.

2.2 Further examples of particularly preferred polyacrylates are described in the European patent application EP-A-0 767 185 and the American patents U.S. Pat. Nos. 5,480,493, 5,475,073 or 5,534,598.

2.3 Further examples of particularly preferred polyacrylates are sold under the brand name Joncryl$^R$, such as, for instance, Joncryl$^R$ SCX 912 and 922.5.

2.4 Further examples of particularly preferred polyacrylates are those obtainable by polymerizing (a1) from 10 to 51% by weight, preferably from 25 to 41% by weight, of 4-hydroxy-n-butyl acrylate or methacrylate or a mixture thereof, but especially 4-hydroxy-n-butyl acrylate, (a2) from 0 to 36% by weight, preferably from 0.1 to 20% by weight, of a hydroxyl-containing ester of acrylic acid or of methacrylic acid other than (a1), or a mixture thereof, (a3) from 28 to 85% by weight, preferably from 40 to 70% by weight, of an aliphatic or cycloaliphatic ester of methacrylic acid having at least four carbon atoms in the alcohol residue, other than (a1), (a2), or a mixture of such monomers, (a4) from 0 to 3% by weight, preferably from 0.1 to 2% by weight, of an ethylenically unsaturated carboxylic acid or a mixture of such acids, and (a5) from 0 to 20% by weight, preferably from 5 to 15% by weight, of an unsaturated monomer other than (a1), (a3) and (a4), or a mixture of such monomers, to give a polyacrylate having a hydroxyl number of from 60 to 200, preferably from 100 to 160, an acid number of from 0 to 35 and a number-average molecular weight $M_n$ of from 1500 to 10 000, the composition of component (a3) being chosen such that polymerization of this component (a3) alone gives a polymethacrylate with a glass transition temperature of from +10 to +100° C., preferably from +20 to +60° C.

Examples of suitable components (a2) are hydroxyalkyl esters of acrylic acid and methacrylic acid such as hydroxyethyl or hydroxypropyl acrylate or methacrylate, the choice being made such that polymerization of this component (a2) alone gives a polyacrylate with a glass transition temperature of from 0 to +80° C., preferably from +20 to +60° C.

Examples of suitable components (a3) are aliphatic esters of methacrylic acid having four to 20 carbon atoms in the alcohol residue such as n-butyl, isobutyl, tert-butyl, 2-ethylhexyl, stearyl and lauryl methacrylate; or cycloaliphatic esters of methacrylic acid on account of cyclohexyl methacrylate.

Examples of suitable components (a4) are acrylic acid and/or methacrylic acid.

Examples of suitable components (a5) are vinylaromatic hydrocarbons such as styrene, alpha-alkylstyrene or vinyltoluene; amides of acrylic acid and methacrylic acid such as methacrylamide and acrylamide; nitriles of acrylic acid and methacrylic acid; vinyl ethers or vinyl esters, the composition of this component (a5) preferably being so apt that polymerization of components (a5) alone gives a polyacrylate with a glass transition temperature of from +70 to +120° C., in particular from +80 to +100° C.

2.5 The preparation of these polyacrylates is general knowledge and is described, for example, in the standard work Houben-Weyl, Methoden der organischen Chemie, $4^{th}$ edition, volume 14/1, pages 24 to 255, 1961.

3. Polyester resins which are preparable by reacting (a1) at least one cycloaliphatic or aliphatic polycarboxylic acid, (a2) at least one aliphatic or cycloaliphatic polyol containing more than two hydroxyl groups in the molecule, (a3) at least one aliphatic or cycloaliphatic diol and (a4) at least one aliphatic, linear or branched saturated monocarboxylic acid in a molar ratio of (a1):(a2):(a3):(a4)=1.0:0.2 to 1.3:0.0 to 1.1:0.0 to 1.4, preferably 1.0:0.5 to 1.2:0.0 to 0.6:0.2 to 0.9 to give a polyester or alkyd resin.

Examples of suitable components (a1) are hexahydrophthalic acid, 1,4-cyclohexanedicarboxylic acid, endomethylenetetrahydrophthalic acid, oxalic acid, malonic acid, succinic acid, glutaric acid, adipic acid, pimelic acid, suberic acid, azelaic acid or sebacic acid.

Examples of suitable components (a2) are pentaerythritol, trimethylolpropane, triethylolethane and glycerol.

Examples of suitable components (a3) are ethylene glycol, diethylene glycol, propylene glycol, neopentyl glycol, 2-methyl-2-propyl-1,3-propane-diol, 2-methyl-2-butyl-1,3-propanediol, 2,2,4-trimethyl-1,5-pentanediol, 2,2,5-trimethyl-1,6-hexanediol, neopentyl glycol hydroxypivalate or dimethylolcyclohexane.

Examples of suitable components (a4) are 2-ethylenehexanoic acid, lauric acid, isooctanoic acid, isononanoic acid or monocarboxylic acid mixtures which are obtained from coconut oil or palm kernel oil.

The preparation of the polyesters and alkyd resins used with preference in accordance with the invention is general knowledge and is described, for example, in the standard work Ullmanns Encyklopädie der technischen Chemie, 3rd edition, volume 14, Urban & Schwarzenberg, Munich, Berlin, 1963, pages 80 to 89 and pages 99 to 105, and also in the following books: "Resines Alkydes-Polyesters" by J. Bourry, Paris, Dunod, 1952, "Alkyd Resins" by C. R. Martens, Reinhold Publishing Corporation, New York, 1961, and "Alkyd Resin Technology" by T. C. Patton, Interscience Publishers, 1962.

4. Polyurethanes as described in the patents EP-A-0 708 788, DE-A-44 01 544 or DE-A-195 34 361.

The resultant oligomeric and high molecular mass reaction products of the invention and the oligomeric and high molecular mass compounds of the invention which contain the allophanate groups II are outstandingly suitable as binders for coating compositions, adhesives and sealing compounds.

Low molecular mass and oligomeric compounds of the invention which contain allophanate groups III are, in particular, amino resins based on melamine and/or benzoguanamine. Examples of suitable amino resins are hexamethylolmelamine, hexamethoxymethylmelamine, tetra-methylolbenzoguanamine, tetramethoxymethylbenzoguanamine or their oligomeric condensation products. In this context, all the methylol and/or methoxymethyl groups of a starting product, or only part thereof, may be converted into allophanate groups III.

These low molecular mass and oligomeric compounds of the invention may be prepared by any desired methods. In accordance with the invention, however, it is of advantage to synthesize them by process B of the invention. For this purpose, the amino resins are reacted in solution or without solvent with alkyl allophanates which in addition to the radicals R of the general formula I may also contain the radicals $R^1$ of the general formula III. It is of advantage in accordance with the invention to conduct the reaction at from 50 to 150° C., preferably from 60 to 130° C. and in particular from 80 to 120° C. A particularly good course of the reaction is ensured by continually removing the water and/or the methanol from the reaction mixture, by vacuum distillation, for example. In order to accelerate the reaction, it is also possible to add a customary and known acidic catalyst such as p-toluenesulfonic acid to the reaction mixture.

Low molecular mass and oligomeric compounds of the invention which contain allophanate groups IV are, in particular, products of reaction of polyisocyanates with hydroxyalkyl and hydroxyaryl allophanates of the general formula VI:

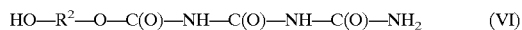

HO—R²—O—C(O)—NH—C(O)—NH—C(O)—NH₂ (VI)

Suitable hydroxyalkyl allophanates VI for use in accordance with the invention contain the above-described radicals R², of which the ethylene and the trimethylene radical and also the 1,4-phenylene radical are particularly advantageous and are therefore used with very particular preference.

Examples of suitable polyisocyanates for use in accordance with the invention are the customary and known polyisocyanates as used, for example, to prepare two-component coating materials, especially those whose isocyanate groups are attached to aliphatic or cycloaliphatic radicals. Examples of advantageous such polyisocyanates are hexamethylene diisocyanate, isophorone diisocyanate, trimethylhexamethylene diisocyanate, dicyclohexylmethane diisocyanates, 1,4-and 1,3-bis(isocyanatomethyl) cycloalkanes, especially 1,4- and 1,3-bis(isocyanatomethyl) cyclohexane, or the adducts of these polyisocyanates with polyols, especially low molecular mass polyols such as trimethylolpropane, or the polyisocyanates derived from these polyisocyanates and containing isocyanurate groups, uretdione groups, allophanate groups and/or biuret groups.

Where only some of the methylol and/or methoxymethyl groups of an amino resin have been converted into allophanate groups III, the low molecular mass and/or oligomeric compounds of the invention that are in question, which contain the allophanate groups III, may be crosslinked with the low molecular mass and/or oligomeric compounds of the invention which contain the allophanate groups IV, or with the oligomeric and/or high molecular mass reaction products of the invention or the oligomeric and high molecular mass compounds of the invention which contain the allophanate groups II. In this way, it is possible to prepare entirely new high-solids coating compositions, adhesives and sealing compounds or films, especially self-supporting paint films.

Particularly advantageous binders, adhesives and sealing compounds of the invention comprise as binders the oligomeric and/or high molecular mass compounds of the invention which contain the allophanate groups II.

Moreover, they comprise the customary and known amino resins and/or the above-described low molecular mass and/or oligomeric compounds of the invention which in which only some of the methylol and/or methoxymethyl groups have been converted into allophanate groups III. Examples of suitable customary and known amino resins and compounds of the invention are those described above.

Besides these crosslinkers, further crosslinkers may also be present. Examples of suitable further crosslinkers are resins or compounds containing siloxane groups, resins or compounds containing anhydride groups, resins or compounds containing epoxide groups, blocked and/or unblocked polyisocyanates and/or tris(alkoxycarbonylamino)-triazines as described in the patents U.S. Pat. No. 4,939,213, U.S. Pat. No. 5,084,541, U.S. Pat. No. 5,288,865 or EP-A-0 604 922.

Depending on the reactivity of the further crosslinker, it may be added directly to the coating compositions, adhesives and sealing compounds of the invention, to give what is known as a one-component system. If, on the other hand, it is a particularly reactive crosslinker, such as a polyisocyanate or an epoxide, it is generally not added to the coating compositions, adhesives and sealing compounds of the invention until shortly before use. The result in this case is what is known as a two-component or multicomponent system.

The coating compositions, adhesives and sealing compounds of the invention may comprise customary and known additives in customary and known, effective amounts.

Examples of suitable additives are polymers, crosslinkers, crosslinking catalysts, initiators, especially photoinitiators, pigments, dyes, fillers, reinforcing fillers, Theological assistants, solvents, wetting agents, dispersants, defoamers, adhesion promoters, additives to improve substrate wetting, additives to improve surface smoothness, flatting agents, leveling agents, film-forming auxiliaries, dryers, antiskinning agents, light stabilizers, corrosion inhibitors, biocides, flame retardants, polymerization inhibitors, especially photoinhibitors, or plasticizers, as are customary and known, for example, in the polymers or coatings sector.

The selection of the additives is guided by the desired profile of properties of the coating compositions, adhesives and sealing compounds of the invention and by their specific end use and may therefore be made by the skilled worker in a simple manner, possibly with the assistance of simple preliminary tests.

The coating compositions of the invention may be present in dispersion or solution in aqueous, aqueous-organic or organic media or may be present as a so-called AND (non-aqueous dispersion). Furthermore, they may be present in fine division in solid form as powder coating materials or in solid forms dispersed in water as powder slurries. The constituents of the coating compositions of the invention that are required in each case are easy for the skilled worker to select on the basis of the given profile of properties (solid, liquid, soluble in organic solvent, water-soluble, etc.).

The coating compositions of the invention may therefore be guided for numerous end uses. For instance, they may be used as powder coating materials in industrial coating, automotive OEM coating or automotive refinish. In these applications, their excellent storage stability is manifested advantageously.

The particular advantages of the coating compositions of the invention are manifested in particular in automotive OEM coating. Here, they may be used as underbody protection, primers, soundproofing compositions, primer-surfacers, stonechip fillers, basecoat materials, solid-color topcoat materials and/or clearcoat materials. With very particular advantage, they are used as clearcoat materials. In this context, they may be applied readily by the wet-on-wet technique. After baking, their high level of compatibility with all customary and known basecoat materials, but especially with the basecoat materials of the invention, is in evidence. The clearcoats of the invention are particularly weathering-stable and scratch-resistant.

EXAMPLES

1. The Preparation of a High Molecular Mass Compound of the Invention Containing Allophanate Groups II 1.1 Preparation of a Hydroxyl-containing Polymeth acrylate The preparation of the polymethacrylate took place in a 4 liter stainless steel reactor with stirrer, reflux condenser, one feed vessel for monomers and one for the initiator. 930 g of solvent naphtha were introduced and heated to 140° C. Over the course of 4.75 hours, the initiator feed, consisting of 167 g of solvent naphtha and 167 g of tert-butyl peroxy-2-ethylhexanoate, was metered in at a uniform rate. Over the course of four hours, the monomer feed, consisting of 348 g of ethylhexyl acrylate, 348 g of ethylhexyl methacrylate, 600 g of hydroxyethyl methacrylate and 369 g of styrene, was metered in at a uniform rate. The monomer feed commenced 15 minutes after the initiator feed. During the polymerization, the temperatures were held at 140° C. After postpolymerization for two hours, the reaction mixture was cooled and adjusted to a solids content of 60% by weight using solvent naphtha. The acid number was 4 and the viscosity (original) was 12 dPa.s.

1.2 The Transallophanatization of the Hydroxyl-containing Polymethacrylate With Ethyl Allophanate 469.03 parts of the hydroxyl-containing polyacrylate in accordance with example 1.1 (60% strength in solvent naphtha), 102.4 parts of ethyl allophanate and 36.7 parts of cyclohexane were charged to an appropriate steel reactor and heated to 130° C. When they had reached this temperature, 1.0 parts of triisodecyl phosphite and 7.4 parts of solvent naphtha were added individually. The resultant reaction mixture was heated at 130° C. for three hours.

Subsequently, 0.5 parts of dibutyltin dioxide and 7.4 parts of solvent naphtha were added and the reaction mixture was stirred at 130° C. for a further three hours. Following this period, 5 parts of dibutyltin dioxide and 7.4 parts of solvent naphtha were again added. The resultant reaction mixture was stirred at 130° C. for a further three hours.

Subsequently, volatile reaction products were removed under vacuum at 115° C. and the resultant solution of the polyacrylate of the invention containing the allophanate groups II was adjusted to a solids content of 60% by weight using a mixture of methoxypropyl acetate and pentyl acetate. The hydroxyl number (OHN) of the product was below 5.

1.3 The Preparation and the Technical Testing of a Coating Composition of the Invention 64.8 parts of the binder of the invention in accordance with example 1.2, 9.5 parts of a customary and known amino resin (Cymel 327; American cyanamid), 1.6 parts of Tinuvin$^R$ 384 (UV absorber; Ciba Geigy), 0.8 parts of Tinuvin$^R$ 123 (free-radical scavenger; Ciba Geigy), 1.6 parts of Nacure$^R$ 4575 (catalyst; King Industries), 1.0 parts of a commercially customary leveling additive, dissolved in 0.2 parts of xylene, 3.4 parts of n-butanol, 2.1 parts of butyl glycol acetate and 14.1 parts of solvent naphtha was mixed with one another. This gave a clearcoat material which showed no increase in viscosity after 16 hours at 60° C. or after 28 days at 40° C. This demonstrated its excellent storage stability.

The clearcoat material of the invention was applied using a gravity flow cup gun (efflux viscosity: 28s DIN 4 cup) to test panels which had been coated with a customary and known electrocoat (20 micrometers), a customary and known primer-surfacer (31 micrometers) and a customary and known basecoat (17 micrometers). In this case, the basecoat material was applied prior to the application of the clearcoat material and was flashed off at room temperature for ten minutes before the clearcoat material was applied.

Following its application, the clearcoat material was likewise flashed off for ten minutes at room temperature. Subsequently, the basecoat and the clearcoat were baked at 140° C. for twenty minutes. The resultant clearcoat had a film thickness of 28 micrometers.

Technical Tests:

The following technical tests were carried out on the test panels coated with the clearcoat material of the invention.

1. BART Test (Chemical Resistance)

The BART (BASF ACID RESISTANCE TEST) was used to determine the resistance of coated surfaces to acids, alkalis and water droplets. After baking, the coating was exposed to further temperature stresses in a gradient oven (30 min at 40° C., 50° C., 60° C. and 70° C.). Before this, the test substances (1%, 10%, 36% strength sulfuric acid; 6% strength sulfurous acid; 10% strength hydrochloric acid; 5% strength sodium hydroxide solution; DI (i.e., deionized) water—1,2,3 or 4 drops) were applied in a defined manner using a metering pipette. Following the action of the substances, they were removed under running water and the damage was assessed visually after 24 h in accordance with a predetermined scale:

| Score | Appearance |
|---|---|
| 0 | no defects |
| 1 | slight marking |
| 2 | marking/dulling/no softening |
| 3 | marking/dulling/shade change/softening |
| 4 | cracks/incipient etching |
| 5 | clearcoat removed |

Each individual marking (spot) was evaluated and the result for each coating was recorded in appropriate form (e.g., score totals for one temperature).

The results can be found in table 1.

TABLE 1

Result of technical testing by the BART test

| | Clearcoat material of the invention | | |
|---|---|---|---|
| Temperature (° C.) | 40 | 50 | 60 |
| $H_2SO_4$ 1% | 0 | 0 | 0 |
| $H_2SO_4$ 10% | 0 | 0 | 0 |
| $H_2SO_4$ 36% | 0 | 0 | 0 |
| HCl 10% | 0 | 0 | 0 |
| $H_2SO_3$ 5% | 0 | 0 | 0 |
| NaOH 5% | 0 | 0 | 0 |
| DI water 1 | 0 | 0 | 1 |
| DI water 2 | 0 | 0 | 0 |
| DI water 3 | 0 | 0 | 0 |
| DI water 4 | 0 | 0 | 0 |
| Total acid | 0 | 0 | 0 |
| Total water | 0 | 0 | 1 |

2. Sand Test and Brush Test (Scratch Resistance)

2.1 Sand Test

This test method tests the resistance (scratch resistance) of film surfaces (clearcoats and topcoats) to scratches caused by wash brushes. The method is a good imitation of the stress undergone by a film surface in a wash installation.

In the sand test, the film surface was subjected to sand (20 g of quartz silver sand 1.5–2.0 mm). The sand was placed in a polyethylene beaker (with its base cut off flat) which was fastened firmly to the test panel. The test panels used were the same ones as described above in the brush test. Using a motor drive, the panel with the beaker and the sand was set in shaking movements. The movements of the loose sand caused damage to the film surface (100 double strokes in 22 s). Following sand exposure, the test surface was cleaned of abraded material, wiped off carefully under a jet of cold water and then dried using compressed air. The gloss to DIN 67530 was measured before and after damage, at 20°.

The results are given in table 2.

2.2 Brush Test

The scratch resistance of the cured coatings was assessed with the aid of the BASF brush test described in FIG. 2 on page 28 of the article by P. Betz and A. Bartelt, Progress in Organic Coatings, 22 (1993), pages 27–37, albeit with modification in respect of the weight used (2000 g instead of the 280 g specified therein), assessment taking place as follows:

In the test, the film surface was damaged using a mesh fabric loaded with a mass. The mesh fabric and the film surface were wetted copiously with a laundry detergent solution. The test panel was moved backward and forward under the mesh fabric in reciprocal movements by means of a motor drive.

The test panels were prepared by applying first an electrocoat with a film thickness of 18–22 μm, then a primer-surfacer with a film thickness of 35–40 μm, then a black basecoat with a film thickness of 20–25 μm, and finally the clearcoat of the invention with a film thickness of 40–45 μm, each of which were cured. Following application of the coating materials, the panels were stored at room temperature for at least 2 weeks before testing was carried out.

The test specimen was an eraser (4.5×2.0 cm, broad side perpendicular to the direction of scratching) covered with nylon mesh fabric (no. 11, 31 μm mesh size, Tg 50° C.). The applied weight was 2000 g.

Prior to each test, the mesh fabric was replaced, with the running direction of the fabric meshes parallel to the direction of scratching. Using a pipette, approximately 1 ml of a freshly stirred 0.25% strength Persil solution was applied in front of the eraser. The rotary speed of the motor was adjusted so that 80 double strokes were performed within a period of 80 s. After the test, the remaining washing liquid was rinsed off with cold tap water and the test panel was blown dry using compressed air. The gloss to DIN 67530 was measured before and after damage (measurement direction perpendicular to the direction of scratching).

The results of the test are likewise given in table 2.

TABLE 2

Results of the sand test and of the brush test

| Gloss values[a] | Clearcoat of the invention Sand test | Clearcoat of the invention Brush test |
|---|---|---|
| Initial gloss | 92 | 90 |
| Residual gloss | 60 | 58 |
| Gloss after 2 h, 40° C. | 64 | 61 |
| Gloss after 2 h, 60° C. | 65 | 64 |

[a]measured at 20° C.

The results of table 2 demonstrate the high scratch resistance of the clearcoat of the invention and its good reflow behavior.

3. Cross-cut Test

The cross-cut test was carried out in accordance with DIN ISO 2409:1994-10. No delamination was observed (GT-01), which demonstrates the excellent adhesion of the clearcoat of the invention to the basecoat.

What is claimed is:

1. An allophanate group-containing compound comprising
    one or more allophanate groups selected from the group consisting of —O—C(O)—NH—C(O)—NH$_2$, —CH$_2$—NH—C(O)—NH—C(O)—OR$^1$, —O—R$^2$—O—C(O)—NH—C(O)—NH$_2$, and mixtures thereof, wherein R$^1$ is selected from the group consisting of alkyl groups, cycloallkyl groups, aryl groups, and mixtures thereof, and R$^2$ is selected from the group consisting of linear alkanediyl groups, branched alkanediyl groups, cyloalcanediyl groups, arylene radicals, and mixtures thereof, and
    the tranallophanatization residue of a nucleophile comprising at least two primary and/or secondary hydroxy groups and which is selected from the group consisting of poly(meth)acrylates, polyesters, polyrethanes, acrylated polyurethanes, acrylated polyesters, polylactones, polycarbonates, polyethers, (meth)acrylatediols, polyureas, oligomeric polyols, and mixtures thereof.

2. A method of using the compounds of claim 1, comprising
    incorporating said compounds into compositions selected from the group consisting of coating compositions, adhesives, sealing compounds, films, and mixtures thereof.

3. The method of using the compounds of claim 2 comprising incorporating said compounds as crosslinkers.

4. Compositions comprising the compounds of claim 1.

5. A process for preparing the compounds of claim 1 comprising the transallophanatization of nucleophiles with alkyl and aryl allophanates.

6. The compounds of claim 1 wherein R$^1$ comprises one or more groups selected from the group consisting of essentially inert groups which do not react with crosslinking agents and free hydroxyl groups.

7. The compounds of claim 1 wherein R$^2$ comprises one or more grops elected from the group consisting of essentially inert groups which do not react with crosslinking agents and free hydroxyl groups.

8. The compounds of claim 1 which have from 3 to 10 repeating identical basic building blocks.

9. The compounds of claim 1 which have more than 10 repeating basic building blocks.

10. The compositions of claim 4 which are selected from the group consisting of coating compositions, film forming compositions, adhesive compositions, sealing compounds, and mixtures thereof.

11. A process for preparing compounds comprising lateral and/or terminal allophanate groups, comprising
    reacting polyisocyanates with hydroxy functional allophanic esters selected from the group consisting of alkyl allophanates, cycloalkyl allophanates, aryl allophanates, and mixtures thereof.

12. Compounds comprising lateral and/or terminal allophanate groups, comprising the reaction product of allophanic esters selected from the group consisting of alkyl allophanates, cycloalkyl allophanates, aryl allophanates, and mixtures thereof with nucleophilic compounds, wherein the compounds have from 3 to 10 repeating identical basic building blocks.

13. Compositions comprising the compounds of claim 12.

14. Compositions according to claim 13, selected from the group consisting of coating compositions, film forming compositions, adhesive compositions, sealing compounds, and mixtures thereof.

15. Compounds comprising lateral and/or terminal allophanate groups, comprising the reaction product of allophanic esters selected from the group consisting of alkyl allophanates, cycloalkyl allophanates, aryl allophanates, and mixtures thereof with nucleophilic compound, wherein the compounds have more than 10 repeating identical basic building blocks.

16. Compositions comprising the compounds of claim 15.

17. Compositions according to claim 16, selected from the group consisting of coating compositions, film forming compositions, adhesive compositions, sealing compounds, and mixtures thereof.

* * * * *